(12) United States Patent
Nishio et al.

(10) Patent No.: US 6,695,788 B2
(45) Date of Patent: Feb. 24, 2004

(54) METHODS FOR MEASUREMENT OF HEMODYNAMICS

(75) Inventors: Ryosuke Nishio, Kyoto (JP); Akira Matsumori, Mino (JP)

(73) Assignees: Kansai Technology Licensing Organization Co., Ltd., Kyoto-fu (JP); Medical Microtechnology, Inc., Kyoto-fu (JP)

( * ) Notice: Subject to any disclaimer, the term of this patent is extended or adjusted under 35 U.S.C. 154(b) by 0 days.

(21) Appl. No.: 10/188,698

(22) Filed: Jul. 1, 2002

(65) Prior Publication Data

US 2003/0093000 A1 May 15, 2003

(30) Foreign Application Priority Data

Jul. 2, 2001 (JP) ........................................ 2001-200975

(51) Int. Cl.[7] .............................. A61B 5/02; A61B 19/00
(52) U.S. Cl. ........................ 600/486; 600/485; 600/507; 128/898
(58) Field of Search ................................. 600/486, 481, 600/485, 507; 128/898

(56) References Cited

U.S. PATENT DOCUMENTS

| | | | | |
|---|---|---|---|---|
| 4,682,603 A | * | 7/1987 | Franz | 600/374 |
| 4,955,382 A | * | 9/1990 | Franz et al. | 600/375 |
| 4,979,510 A | * | 12/1990 | Franz et al. | 600/374 |
| 6,101,412 A | * | 8/2000 | Duhaylongsod | 607/2 |

OTHER PUBLICATIONS

Georgakoupoulos et al. / U.S.A. / Am J Physiol. / 274: H1416–H1422 / 1998.
Georgakoupoulos et al. / U.S.A. / Nat Med / 5: 327–330 / 1999.
Murphy et al. / U.S.A. / Science / 287:488–491 / 2000.
Georgakoupoulos et al. / U.S.A. / Am J Physiol Circ Physiol / 279: H443–H450 / 2000.
Hoit et al. / U.S.A. / Am J Physiol. / 273: H2528–H2533 / 1997.
Yang et al. / U.S.A. / Am J Physiol. / 277: H1906–H1913 / 1999.
Feldman et al. / U.S.A. / Am J Physiol Heart Circ Physiol / 279: H1698–H1707 / 2000.
Esposito et al. / U.S.A. / Circulation / 105: 85–92 / Jan. 2002.

(List continued on next page.)

Primary Examiner—Max F. Hindenburg
Assistant Examiner—Navin Natnithithadha
(74) Attorney, Agent, or Firm—Knobbe Martens Olson & Bear LLP

(57) ABSTRACT

A method for measuring hemodynamics of an experimental animal enabling repeated measurements, the method comprising the following steps:

(i) ligating at least two parts of an artery, between which a part to be incised is located, of the experimental animal, the parts comprising at least one proximal ligated part and at least one distal ligated part, and then incising a part between the ligated parts;

(ii) inserting through the incised part a blood pressure-volume simultaneously measuring catheter provided with multiple conductance electrodes and at least one pressure sensor;

(iii) loosening the distal ligated part so as to allow an insertion of the catheter and not to cause bleeding in the opened part;

(iv) further inserting the catheter so as to introduce the multiple conductance electrodes and the pressure sensor(s) into the heart ventricle; and (v) simultaneously measuring pressure and volume of the heart.

7 Claims, 9 Drawing Sheets

Volume calibration of the conductance catheter

OTHER PUBLICATIONS

Eucker et al. / U.S.A. / J Appl Physiol / 92: 323–330 / Jan. 2002.
Gross et al. / U.S.A. / Journal of Hypertension / vol. 19, No. 5, 967–976 / 2001.
Lips et al. / Netherlands / PV–LOOPS / 40 / Jan. 2002.
Tschoepe et al. / Netherlands / PV–LOOPS / 76 / Jan. 2002.
Lips et al. / Netherlands / PV–LOOPS / 126 / Jan. 2002.
Michele et al. / U.S.A. / Circulation Research / 91: 255–262 / Aug. 9, 2002.
Lipskaia et al. / U.S.A. / Circulation Research / 86: 795–801 / Apr. 14, 2000.
Ju et al. / U.S.A. / PNAS / vol. 98, No. 13, 7469–7474 / Jun. 19, 2001.
Hart et al. / U.S.A. / Am J Physiol Heart Circ Physiol / 281: H1938–H1945 / Nov. 2001.
Oliver et al. / U.S.A. / Proc. Natl. Acad. Sci. USA / vol. 94, 14730–14735 / Dec. 1997.
Kumar et al. / U.S.A. / Proc. Natl. Acad. Sci. USA / vol. 94, 4406–4411 / Apr. 1997.
Gottshall et al. / U.S.A. / Proc. Natl. Acad. Sci. USA / vol. 94, 4710–4715 / Apr. 1997.
Trabold et al. / U.S.A. / Hypertension / 40: 90–95 / Jul. 2002.
Feldman et al. / U.S.A. / Am J Physiol Heart Circ Physiol / 279: H1411–H1420 / 2000.
Esposito et al. / U.S.A. / Am J Physiol Heart Circ Physiol / 279: H3101–H3112 / 2000.
Cho et al. / U.S.A. / Circulation / 99: 2702–2707 / May 25, 1999.
Rockman et al. / U.S.A. / Proc. Natl. Acad. Sci. USA / vol. 88, 8277–8281 / Sep. 1991.
Kohout et al. / U.S.A. / Circulation / 104: 2485–2491 / Nov. 13, 2001.
Wettschureck et al. / U.S.A. / Nature Medicine / vol. 7, No. 11, 1236–1240 / Nov. 2001.
Harding et al. / U.S.A. / PNAS / vol. 98, No. 10, 5809–5814 / May 8, 2001.
Rockman et al. / U.S.A. / Proc. Natl. Acad. Sci. USA / vol. 95, 7000–7005 / Jun. 1998.
Barouch et al. / U.S.A. / Nature / vol. 416, 337–340 / Mar. 21, 2002.
Iaccarino et al. / U.S.A. / Journal of the American College of Cardiology / vol. 38, No. 2, 534–540 / Aug. 2001.
Shi et al. / U.S.A. / Alcohol / 24: 197–204 / 2001.
Dorn II et al. / U.S.A. / Proc. Natl. Acad. Sci. USA / vol. 96, 6400–6405 / May 1999.
Meneton et al. / U.S.A. / PNAS / vol. 98, No. 5, 2634–2639 / Feb. 27, 2001.
Liao et al. / U.S.A. / PNAS / vol. 98, No. 21, 12283–12288 / Oct. 9, 2001.
Condorelli et al. / U.S.A. / PNAS / vol. 99, No. 19, 12333–12338 / Sep. 17, 2002.
Kass et al. / U.S.A. / Circ Res. / 82: 519–522 / 1998.
Semsarian et al. / U.S.A. / Journal of Clinical Investigation / vol. 109, No. 8, 1013–1020 / Apr. 2002.
McConnell et al. / U.S.A. / Circulation Research / 88: 383–389 / Mar. 2, 2001.
Paolocci et al. / U.S.A. / Am J Physiol Heart Circ Physiol / 279: H1982–H1988 / 2000.
Kubota et al. / U.S.A. / J Mol Cell Cardiol / 30, 357–363 / 1998.
Stull et al. / U.S.A. / J Mol Cell Cardiol / 32, 2035–2049 / 2000.
Takaoka et al. / U.S.A. / Am J Physiol Heart Circ Physiol / 282: H2190–H2097 / Jun. 2002.
Kawada et al. / U.S.A. / PNAS / vol. 99, No. 2, 901–906 / Jan. 22, 2002.
Engelhardt et al. / U.S.A. / Proc. Natl. Acad. Sci. USA / vol. 96, 7059–7064 / Jun. 1999.

* cited by examiner

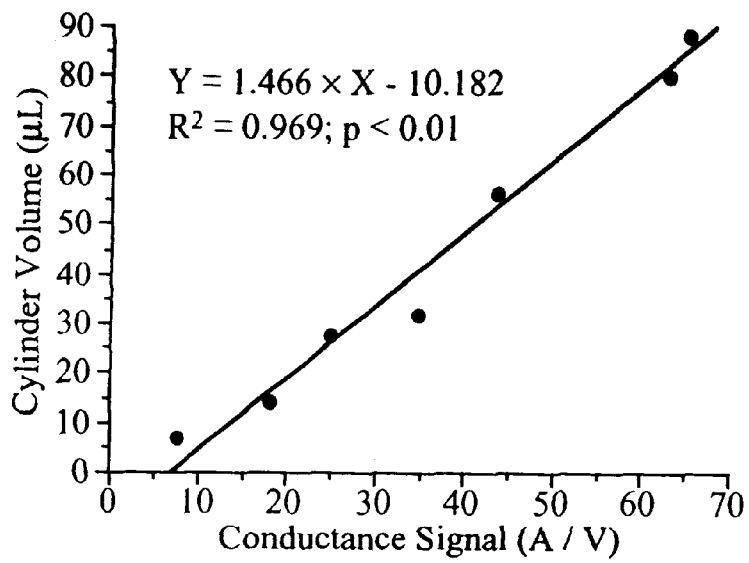
Volume calibration of the conductance catheter
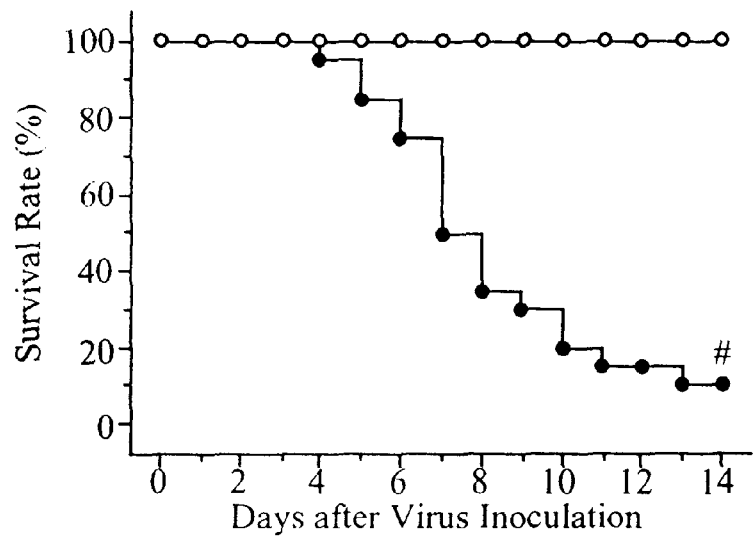
Cumulative survivals of experimental groups

Pressure-volume relations, LV pressure, and dP/dt.

Pressure-volume relations, LV pressure, and dP/dt (Continued).

Pressure-volume relations, LV pressure, and dP/dt (Continued).

PRSW relationship and (dP/dt$_{max}$)/EDV.

Evolution of hemodynamic variables.

Evolution of hemodynamic variables (Continued).

Evolution of hemodynamic variables (Continued).

Pathologic manifestations during 3 phases of acute EMCV-induced myocarditis

METHODS FOR MEASUREMENT OF HEMODYNAMICS

FIELD OF THE INVENTION

This invention relates to a method for measuring hemodynamics (pressure and volume of the heart) to evaluate pharmacological and therapeutic effects and the like in animal experiments.

DESCRIPTION OF RELATED ART

Methods for measuring pressure-volume relationship regarding hemodynamics in animal experiments have been known.

In the prior art, especially in a small experimental animal such as a mouse and the like, hemodynamics have been measured by opening the chest of the animal, sticking a measuring instrument such as a needle into the heart of the mouse, and inserting a catheter through the needle. However, since this method is invasive, hemodynamics under physiological conditions cannot be measured.

Especially, an experimental animal for genetic manipulation (a mutant) as a model with a serous disease is essentially vulnerable to invasions and tends to easily die. Therefore, there have been disadvantages that for such an experimental animal, it is difficult to used the prior art methods, like opening chest of the animal and directly puncturing the heart of the animal. Moreover, even though the prior art methods are used, they have a disadvantage that it is not easy to obtain correctly measured values from an experimental animal that has been weakened by invasions.

Also, since the prior art methods require to open the chest of the experimental animal once for each measurement, they can measure hemodynamics only once in an individual animal. Hence, it was impossible to investigate the time-course of hemodynamics by repeatedly measuring required values in a single animal.

An object of the invention is to provide an effective method for measuring hemodynamics to evaluate pharmacological and therapeutic effects and so on in animal experiments.

BRIEF DESCRIPTION OF THE SEVERAL VIEWS OF THE DRAWING

FIG. 1 shows a volume calibration of the conductance catheter as an embodiment of the present invention.

FIG. 2 shows cumulative survivals of experimental groups in Example 1.

BRIEF SUMMARY OF THE INVENTION

Figure 3:
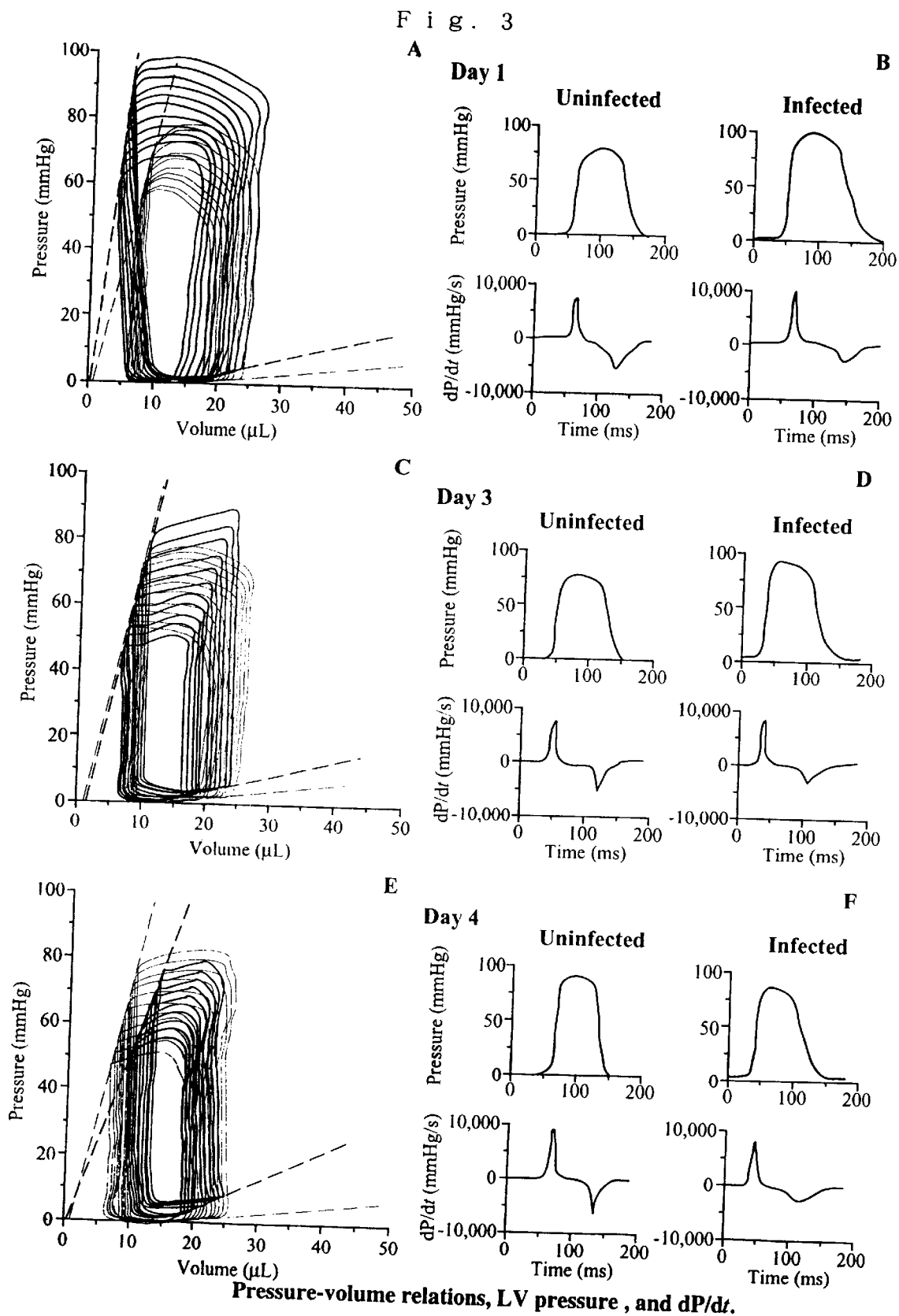
FIG. 3 shows pressure-volume relations, LV pressure and dP/dt curves in control versus infected groups, obtained in Example 1.

As a result of extensive study in light of the above-mentioned problems, the inventors found that it is possible to provide a method for simultaneously measuring hemodynamics, which is effective and allows an individual experimental animal to be repeatedly measured, by using a blood pressure-volume simultaneously measuring catheter provided with multiple, for example four conductance electrodes and at least one pressure sensor. The present invention shown below has been accomplished based on this novel finding.

1. A method for measuring hemodynamics of an experimental animal enabling repeated measurements, the method comprising the following steps:
   (i) ligating at least two parts of an artery, between which a part to be incised is located, of the experimental animal, the parts comprising at least one proximal ligated part and at least one distal ligated part, and then incising a part between the ligated parts;
   (ii) inserting through the incised part a blood pressure-volume simultaneously measuring catheter provided with multiple conductance electrodes and at least one pressure sensor;
   (iii) loosening the proximal ligated part so as to allow an insertion of the catheter and not to cause bleeding in the opened part;
   (iv) further inserting the catheter so as to introduce the multiple conductance electrodes and the pressure sensor(s) into the heart ventricle; and
   (v) simultaneously measuring pressure and volume of the heart.
2. The method according to Item 1, further comprising the following steps:
   (vi) pulling the catheter until a tip of the catheter is positioned between the proximal ligated part and the incised part;
   (vii) ligating the proximal ligated part to such an extent as to prevent bleeding in the opened part after the catheter is completely pulled out;
   (viii) pulling out the catheter and suturing the opened part; and
   (ix) untying the proximal ligated part and the distal ligated part.
3. The method according to Item 1, wherein the artery of the experimental animal is cranial to the heart.
4. The method according to Item 3, wherein the artery cranial to the heart is a carotid artery.
5. The method according to Item 1, further comprising a step of investigating time-course of hemodynamics by repeatedly measuring hemodynamics in a single individual animal.
6. The method according to Item 1, wherein in the step (i), ligating three parts of the artery, among which a part to be incised is located, the three parts being two proximal ligated parts and a distal ligated part, and in the step (iii), loosening the two proximal ligated parts.
7. The method according to Item 1, wherein the experimental animal is a mouse.

DETAILED DESCRIPTION OF THE INVENTION

Experimental animals that can be subjected to the measurement according to the present invention, include a mouse, a rat, a hamster, a rabbit and so on. A mouse and a rat are preferable, and a mouse is more preferable.

A method for measuring hemodynamics according to the present invention can contribute to a specific disease study by using an experimental animal of a disease model as a measurement object. Such a disease model can be properly and desirably selected, and examples are a genetic disease, a disease caused by infection of virus, bacteria and the like, a disease caused by medication, etc. Specifically, exemplified is an animal model of myocarditis, cardiac infarction, hypertensive heart disease, dilated cardiomyopathy or hypertrophic cardiomyopathy, a transgenic mouse, or a knockout mouse (for example, a PD-1 knockout mouse), or the like.

If the experimental animal whose hemodynamics to be measured has a blood vessel with the same diameter as that of a catheter used, the hemodynamics can be measured according to the present invention because of blood vessel dilatation. For example, when a mouse has an artery, cranial to the heart, with a diameter of 0.4 mm, a catheter with a diameter of 0.4 mm may be introduced through an incised part of 0.25 mm width.

Conditions under which hemodynamics are repeatedly measured according to the present invention are not specifically limited. When hemodynamics are measured more than once in an individual animal, for example, locations through which a catheter is inserted may be identical or different, wherein the locations are not specifically restricted to have certain relations among them. Intervals of measurements are optional, and the following measurement can be done anytime.

A measuring device used in the present invention is not specifically limited, as long as it can measure hemodynamics through a blood vessel of a desired experimental animal. For example, one of the most commonly used is Millar 1.4 Fr catheter (SPR-719, Millar Instruments, Houston, Tex., USA) composed of four conductance electrodes and a micromanometer. A distance between the conductance sensor electrodes is 4.5 mm.

A catheter used in the present invention comprises multiple and even conductance electrodes for measuring volumes and (a) pressure sensor(s) for measuring pressure. The catheter is provided with at least one of the pressure sensors for measuring pressure, usually one pressure sensor.

A blood vessel through which a catheter is inserted in the present invention is an artery, preferably a carotid artery and an artery that comprises a brachial artery and is cranial to the heart.

A ligating means according to the present invention is preferably a ligation by a ligature, and a blood vessel clip for neurosurgery may also be used. As the ligature, silk suture and nylon suture are exemplified, and silk suture is preferable. A size of the suture is preferably 4-0, for example.

In the invention described in Item 1 above, the step of "(ii) inserting through the opened part a blood pressure-volume simultaneously measuring catheter provided with multiple conductance electrodes and at least one pressure sensor" can be conducted by inserting a catheter until a tip of the catheter reaches the proximal ligated part.

Regarding the invention described in Item 1 above, in the step of "(iii) loosening the proximal ligated part so as to allow an insertion of the catheter and not to cause bleeding in the opened part," repeating (a) gradually loosening the ligated part and (b) inserting the catheter makes it possible to loosen the proximal ligated part to such an extent as not to cause bleeding. Although this operation can be done even when there is one proximal ligated part, it is more preferable, especially in a small experimental animal such as a mouse, to make two proximal ligated parts and gradually loose the two ligated parts.

In the invention described in Item 2 above, the step of "(vii) ligating the proximal ligated part to such an extent as not to cause bleeding in the opened part after the catheter is completely pulled out" can be done by alternately repeating (a) pulling the catheter in an extremely gradual way and (b) ligating with adjusting to a diameter of the catheter because the tip of the catheter is thinner than the other part far from the tip.

BEST MODE FOR CARRYING OUT THE INVENTION

Hereinafter, methods for measuring hemodynamics used in the present invention are explained by an example of a murine model of cardiomyopathy as a disease model to be investigated. Note that it is easy for a person having ordinary skill in the art to conduct the present invention by replacing each composition mentioned in the explanation below with another having similar functions.

EXAMPLE 1

Viral myocarditis is an important cause of congestive heart failure and may lead to dilated cardiomyopathy. However, the hemodynamic changes associated with its acute phase have not been analyzed in detail. This study, performed in a murine model of encephalomyocarditis virus myocarditis, used a new Millar 1.4-Fr conductance-micromanometer system for the in vivo determination of the left ventricular (LV) pressure-volume relationship (PVR).

Methods
(1) Conductance Catheter System Design

We used the Millar 1.4 Fr catheter (SPR-719, Millar Instruments, Houston, Tex., USA) composed of 4 conductance electrodes and a micromanometer. The distance between the conductance sensor electrodes is 4.5 mm. The conductance system and the pressure transducer controller [Integral 3 (VPR-1002), Unique Medical Co., Tokyo, Japan] were set at a frequency of 20 kHz, the full-scale current selected at 20 $\mu$A, and the pressure transducer at 5 $\mu$V/V/100 mmHg. The pressure-volume loops and intracardiac electrocardiogram were monitored on-line, and the conductance, pressure, and intracardiac electrocardiographic signals were digitized at 2 kHz, stored on disk, and analyzed with Integral 3 software (Unique Medical Co.).

(2) Surgical Procedure

Mice were anesthetized with a mixture of ketamine, 100 mg/kg, and xylazine, 5 mg/kg, intraperitoneally; additional smaller doses were given occasionally, as needed. The animals were placed in the supine position under a dissecting microscope (model MZ75: Leica Microsystems Wetzlar GmbH, Wetzlar, Germany), and a vertical midline cervical incision was made to expose the trachea by microsurgical techniques. After successful endotracheal intubation, the cannula was connected to a volume cycled rodent ventilator (Shinano Co., Tokyo, Japan) with supplemental oxygen, a tidal volume of 7 $\mu$L/g and a respiratory rate of 140/min. The right carotid artery and external jugular vein were exposed via the same midline incision. To allow the use of a physiologic closed-chest preparation, a 1.4 Fr. SPR-719 Millar catheter was advanced via the right carotid artery into the ascending aorta for measurements of aortic pressure, then inserted into the LV. A substernal transverse incision was made to expose the inferior vena cava. Left ventricular pressure-volume relations were measured by transiently compressing the inferior vena cava, after which the external jugular vein was cannulated with polyethylene tubing (PE-10; Becton Dickinson and Co., Franklin Lakes, N.J., USA) for volume administration. Parallel volume (Vp) of each mouse was calibrated by the injection of 10 μL of hypertonic saline into the external jugular vein.

(3) Measurements of Right Atrial Pressure

Following the measurements of Vp, the PE-10 tubing was replaced by a modified 0.014-in Pressure Wire™ Sensor (Radi Medical System AB, Uppsala, Sweden) for right atrial (RA) pressure measurements. After having removed its distal portion, the pressure wire was inserted through the external jugular vein into the RA, and connected to the Pressure Wire™ Interface. (Radi Medical System AB). The pressure tracings and surface electrocardiogram were monitored on-line [Biomedical Research System(LEG-1000), Nihon Koden Co., Tokyo, Japan]. The RA pressure was measured, and the pressure waveforms and electrocardiogram were digitized at 2 kHz, stored to disk, and analyzed with commercially available software (LEG-1000, Nihon Koden Co., Tokyo, Japan).

(4) Volume Calibration of the Conductance Catheter

The volume calibration of this conductance system was performed as described by Yang et al (Yang et al.; Am J Physiol, 277: 1906–1913(1999)). Briefly, 7 cylindrical holes in a block 1 cm deep and with known diameters ranging from 1.4 to 5 mm were filled with fresh heparinized whole murine blood. An interelectrode distance of 4.5 mm was used to calculate the absolute volume in each cylinder. In this calibration, the linear volume-conductance regression of the absolute volume in each cylinder vs. the raw signals acquired by the conductance catheter was used as the volume calibration formula (FIG. 1).

(5) Analysis of the Signals

All pressure-volume loop data were analyzed with the Integral 3 software (Unique Medical Co.). Indices of contractility and LV stiffness were calculated, including end-systolic pressure volume relationship (ESPVR), endsystolic volume elastance ($E_{es}$), stroke work (SW)-enddiastolic volume (EDV) relation [preload recruitable stroke work (PRSW)], slope of maximum derivative of change in systolic pressure over time ($dP/dt_{max}$)-EDV relation [(dP/$dt_{max}$)/EDV], enddiastolic pressure volume relationship (EDPVR), and enddiastolic volume elastance ($E_{ed}$). $E_{es}$ and $E_{ed}$ were normalized by 100 mg of heart weight (HW). The ventricular-to-vascular coupling ratio was assessed by the arterial elastance ($E_a$)-to-$E_{es}$ ratio ($E_a/E_{es}$). The time constant of isovolumic relaxation (τ) was also calculated by linear regression of $dP/dt_{max}$ vs. pressure from data between the minimum derivative of change in diastolic pressure over time ($dP/dt_{min}$) and 5 mmHg above EDP. Stroke volume (SV), cardiac output (CO), and SW were normalized by body weight (BW) [stroke volume index (SVI), cardiac index (CI), and SW index (SWI), respectively]. The systemic vascular resistance index (SVRI) was calculated by the following equation: SVRI=[mean aortic pressure ($AO_{mean}$)—mean right atrial pressure ($RA_{mean}$))]/CI.

(6) Experimental Infection

A dose of 0.1 mL of the M variant of EMCV diluted in Eagle's modified essential medium (EMEM, Nissui Pharmaceutical Co., Tokyo, Japan) to a concentration of 1,000 plaque-forming units/mL was inoculated intraperitoneally in 32-day-old, 17 g, inbred male DBA/2 mice. A dose of 0.1 mL of phosphate buffered saline (PBS) was inoculated intraperitoneally to uninfected control mice. The day of virus inoculation was defined as day 0.

(7) Time Course of Hemodynamics in Uninfected or Infected Mice

Serial hemodynamic measurements were made in both groups on days 0, 1, 3, 4, 5, 7, 9, 12, and 14, after which the chest was opened, the heart removed, and whole body and heart were weighed.

(8) Survival Experiments

In addition to the hemodynamic measurements, survival rates of uninfected versus infected mice were compared over a 14-day period.

(9) Statistical Analysis

Statistical comparisons were performed by analysis of variance with Bonferroni's multiple comparisons correction or unpaired Student's t-test. The standard volume lines were analyzed by simple linear regression. Survival was analyzed by the Kaplan-Meier method. Values are expressed as mean ±SE. A p value <0.05 was considered significant.

Results (A) Survivals, Body Weights, Heart Weights, and Heart Weight/Body Weight Ratios of Uninfected Versus Infected Mice FIG. 2 shows cumulative survivals of experimental groups in Example 1 (○:uninfected control group (n=10), ●:infected group (n=20), #; p<0.01). X-axis represents days after virus inoculation, and Y-axis does survival rate. Infected mice (n=20) began dying on day 4, and 60% died between day 5 and day 8. Survival of infected mice on day 14 was 10%. In contrast, no uninfected mice (n=10) died during this 14-day period (p<0.01, FIG. 2).

TABLE 1

Hemodynamics of EMCV-infected and uninfected mice based on pressure-volume relations (Means ± SE)

|  | Day 0 | | Day 1 | | Day 3 | |
|---|---|---|---|---|---|---|
|  | Uninfected | Infected | Uninfected | Infected | Uninfected | Infected |
| BW (g) | 17.0 ± 0.1 | 17.1 ± 0.1 | 17.8 ± 0.2 | 17.4 ± 0.3 | 18.6 ± 0.1 | 15.2 ± 0.5# |
| HW (mg) | 80.4 ± 0.7 | 80.8 ± 0.6 | 82.2 ± 1.9 | 82.8 ± 2.7 | 86.2 ± 1.0 | 84.8 ± 1.3 |
| HW/BW | 4.7 ± 0.1 | 4.7 ± 0.1 | 4.6 ± 0.1 | 4.8 ± 0.1 | 4.6 ± 0.1 | 5.6 ± 0.1# |
| HR (min$^{-1}$) | 345 ± 12 | 343 ± 13 | 339 ± 14 | 350 ± 11 | 343 ± 14 | 358 ± 14 |
| ESP (mmHg) | 71.6 ± 2.3 | 71.4 ± 2.3 | 73.0 ± 1.4 | 91.4 ± 3.4# | 74.6 ± 2.4 | 80.1 ± 1.4 |
| EDP (mmHg) | 1.10 ± 0.12 | 1.60 ± 0.24 | 1.10 ± 0.12 | 3.48 ± 0.21# | 1.80 ± 0.20 | 5.04 ± 0.45# |
| ESV (μL) | 9.02 ± 0.19 | 8.96 ± 0.29 | 9.22 ± 0.17 | 6.92 ± 0.86* | 9.54 ± 0.23 | 9.47 ± 0.40 |
| EDV (μL) | 23.68 ± 1.07 | 23.80 ± 1.07 | 24.42 ± 0.92 | 23.45 ± 0.78 | 25.00 ± 0.58 | 23.70 ± 1.09 |
| $dP/dt_{max}$ (mmHg/s) | 7,416 ± 602 | 7,358 ± 558 | 7,772 ± 231 | 10,175 ± 312# | 8,152 ± 449 | 8,644 ± 775 |
| $dP/dt_{min}$ (mmHg/s) | −5,102 ± 610 | −4,887 ± 760 | −5,137 ± 209 | −3,942 ± 315# | −5,094 ± 455 | −3,523 ± 472* |
| $NLE_{es}$ (mmHg/μL · 100 mg) | 7.51 ± 0.35 | 7.23 ± 0.24 | 7.49 ± 0.38 | 11.00 ± 1.26* | 7.48 ± 0.24 | 8.47 ± 1.22 |

TABLE 1-continued

Hemodynamics of EMCV-infected and uninfected mice based on pressure-volume relations (Means ± SE)

| | | | | | | |
|---|---|---|---|---|---|---|
| $NLE_{ed}$ (mmHg/μL · 100 mg) | 0.10 ± 0.01 | 0.10 ± 0.01 | 0.12 ± 0.01 | 0.46 ± 0,06# | 0.15 ± 0.01 | 0.47 ± 0.05# |
| SVRI (mmHg/mL · min · g) | 190.5 ± 16.8 | 190.5 ± 16.8 | 196.0 ± 7.3 | 227.6 ± 11.3* | 203.5 ± 18.0 | 189.6 ± 11.1 |

| | Day 4 | | Day 5 | | Day 7 | |
|---|---|---|---|---|---|---|
| | Uninfected | Infected | Uninfected | Infected | Uninfected | Infected |
| BW (g) | 19.1 ± 0.1 | 14.9 ± 0.5# | 19.5 ± 0.2 | 13.7 ± 0.4# | 20.9 ± 0.1 | 10.6 ± 0.2# |
| HW (mg) | 87.6 ± 1.2 | 88.6 ± 2.2 | 90.2 ± 1.0 | 94.4 ± 1.5* | 93.2 ± 0.7 | 96.8 ± 1.4* |
| HW/BW | 4.6 ± 0.1 | 6.0 ± 0.1# | 4.6 ± 0.1 | 6.9 ± 0.1# | 4.5 ± 0.1 | 9.2 ± 0.1# |
| HR (min$^{-1}$) | 348 ± 10 | 355 ± 5 | 353 ± 7 | 351 ± 12 | 362 ± 15 | 322 ± 19 |
| ESP (mmHg) | 77.6 ± 4.8 | 77.4 ± 1.7 | 79.9 ± 3.0 | 70.4 ± 5.2 | 83.7 ± 3.3 | 62.0 ± 3.7# |
| EDP (mmHg) | 2.80 ± 0.37 | 6.8 ± 0.70# | 2.20 ± 0.20 | 8.10 ± 0.64# | 2.40 ± 0.24 | 20.88 ± 1.17# |
| ESV (μL) | 9.66 ± 0.17 | 13.88 ± 1.02 | 8.96 ± 0.28 | 20.11 ± 0.38# | 9.44 ± 0.51 | 33.58 ± 0.31# |
| EDV (μL) | 25.16 ± 0.48 | 24.94 ± 0.50 | 25.68 ± 0.28 | 30.16 ± 0.71* | 27.06 ± 0.59 | 38.92 ± 0.38# |
| $dP/dt_{max}$ (mmHg/s) | 8,192 ± 136 | 8,114 ± 729 | 8,212 ± 419 | 5,879 ± 217# | 8,382 ± 556 | 4,224 ± 402# |
| $dP/dt_{min}$ (mmHg/s) | −5,916 ± 187 | −3,312 ± 475# | −5,722 ± 185 | −2,587 ± 167# | −6,713 ± 625 | −2,149 ± 425# |
| $NLE_{es}$ (mmHg/μL · 100 mg) | 7.49 ± 0.22 | 4.93 ± 0.70* | 8.15 ± 0.38 | 4.64 ± 0.38# | 8.28 ± 0.28 | 2.26 ± 0.47# |
| $NLE_{ed}$ (mmHg/μL · 100 mg) | 0.17 ± 0.01 | 0.68 ± 0.66# | 0.18 ± 0.01 | 0.74 ± 0.09# | 0.23 ± 0.02 | 1.54 ± 0.37# |
| SVRI (mmHg/mL · min · g) | 212.2 ± 13.1 | 217.6 ± 9.0 | 203.6 ± 20.1 | 205.5 ± 12.9 | 205.4 ± 15.8 | 225.4 ± 11.8 |

| | Day 9 | | Day 12 | | Day 14 | |
|---|---|---|---|---|---|---|
| | Uninfected | Infected | Uninfected | Infected | Uninfected | Infected |
| BW (g) | 21.5 ± 0.1 | 11.2 ± 0.2# | 22.4 ± 0.2 | 13.4 ± 1.0# | 22.8 ± 0.3 | 16.7 ± 0.3# |
| HW (mg) | 94.8 ± 1.0 | 95.6 ± 1.5 | 96.8 ± 0.9 | 99.2 ± 2.3 | 98.2 ± 1.2 | 99.0 ± 1.6 |
| HW/BW | 4.4 ± 0.1 | 8.6 ± 0.2# | 4.3 ± 0.1 | 7.5 ± 0.4# | 4.3 ± 0.1 | 5.9 ± 0.1# |
| HR (min$^{-1}$) | 339 ± 15 | 324 ± 27 | 345 ± 3 | 326 ± 14 | 352 ± 10 | 327 ± 9 |
| ESP (mmHg) | 86.4 ± 2.6 | 70.7 ± 2.2# | 89.0 ± 1.7 | 74.8 ± 2.7* | 93.2 ± 3.2 | 80.7 ± 1.5# |
| EDP (mmHg) | 2.40 ± 0.24 | 18.32 ± 0.60# | 1.10 ± 0.12 | 16.50 ± 0.94# | 1.60 ± 0.24 | 15.46 ± 0.39# |
| ESV (μL) | 9.96 ± 0.27 | 34.26 ± 1.37# | 10.34 ± 0.19 | 36.72 ± 0.96# | 11.00 ± 1.09 | 36.38 ± 0.56# |
| EDV (μL) | 27.56 ± 0.60 | 41.08 ± 1.40# | 28.22 ± 0.77 | 44.60 ± 0.61# | 28.38 ± 0.94 | 47.76 ± 0.95# |
| $dP/dt_{max}$ (mmHg/s) | 9,172 ± 140 | 5,792 ± 372# | 9,332 ± 187 | 8,040 ± 483* | 9,742 ± 317 | 8,256 ± 163# |
| $dP/dt_{min}$ (mmHg/s) | −7,582 ± 287 | −2,916 ± 276# | −8,122 ± 398 | −4,696 ± 422# | −8,498 ± 341 | −5,764 ± 680# |
| $NLE_{es}$ (mmHg/μL · 100 mg) | 8.26 ± 0.62 | 2.50 ± 0.35# | 8.36 ± 0.37 | 2.60 ± 0.58# | 8.42 ± 0.55 | 2.92 ± 0.45# |
| $NLE_{ed}$ (mmHg/μL · 100 mg) | 0.23 ± 0.01 | 0.55 ± 0.12* | 0.24 ± 0.01 | 0.37 ± 0.06 | 0.32 ± 0.03 | 0.36 ± 0.07 |
| SVRI (mmHg/mL · min · g) | 233.5 ± 17.1 | 243.4 ± 13.3 | 242.5 ± 12.8 | 244.1 ± 21.2 | 262.9 ± 15.7 | 248.5 ± 23.9 |

*p < 0.05, #p < 0.01 vs Uninfected Control. N = 5 in each.

Table 1 shows the time course of BW, HW, and HW/BW ratio. The BW of infected mice decreased after day 1, and by day 3, had decreased significantly compared with uninfected control mice. The weight loss was greatest on day 7, and returned toward baseline between day 9 and day 14, though, compared to controls, BW of the infected animals remained significantly lower, up to day 14. The HW of infected mice was significantly greater on days 5 and 7. Consequently, the HW/BW ratio increased after day 1, was significantly greater by day 3, peaked on day 7, then returned toward baseline between day 9 and 14, though remained significantly higher in the infected than uninfected mice.

(B) Time Course of Hemodynamic Function in Uninfected Versus Infected Mice

Table 1 compares multiple indices of hemodynamic function in control versus infected mice between day 0 and day 14. No difference was found between the 2 groups at baseline. Heart rate remained stable in both groups over the 14 days of observation.

Figure 4:
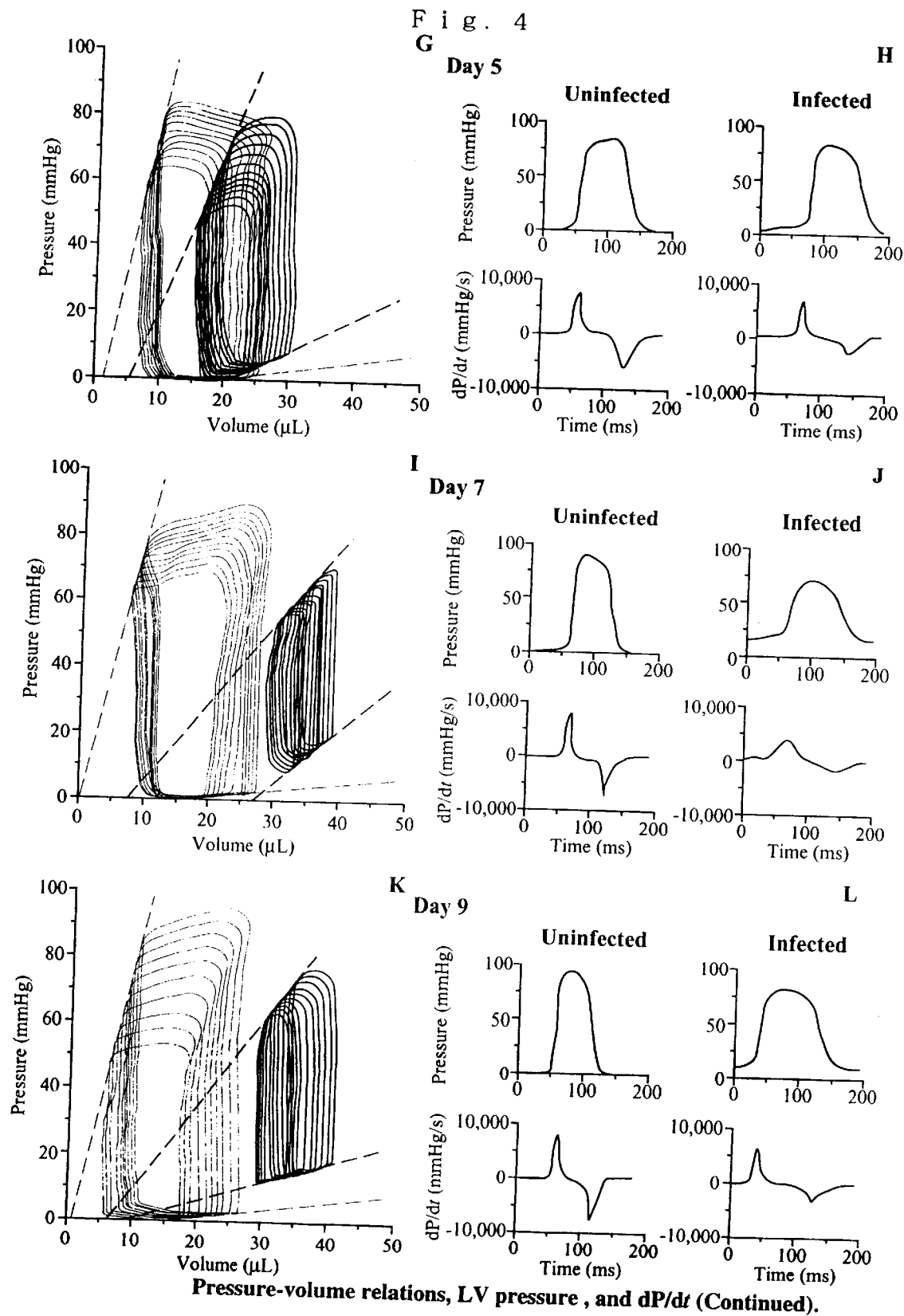
FIG. 4 shows pressure-volume relations, LV pressure and dP/dt curves in control versus infected groups, obtained in Example 1.
Figure 5:
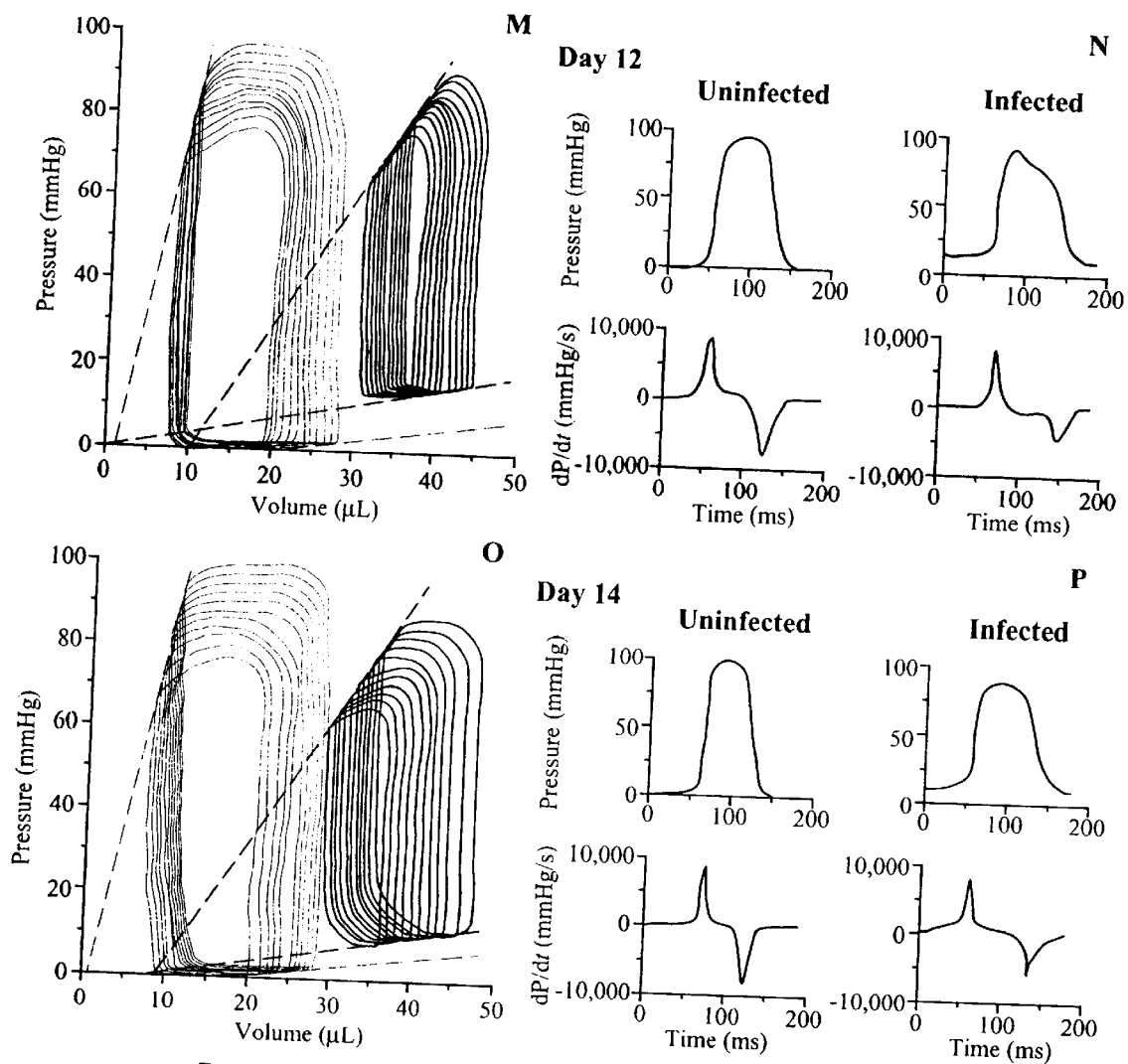
FIG. 5 shows pressure-volume relations, LV pressure and dP/dt curves in control versus infected groups, obtained in Example 1.

FIGS. 3–5 show pressure-volume relations, LV pressure and dP/dt curves in control versus infected groups. A, C, E, G, I, K, M and O represent pressure-volume relations. Thin solid line curves show data from the uninfected control group, and thick solid line curves from the infected group. Dashed lines represent ESPVR and EDPVR. B, D, F, H, J, L, N and P represent LV pressure (upper) and dP/dt curves (lower). A and B pertain to mice on day 1; C and D on day 3; E and F onday 4; G and H on day 5; I and J on day 7; K and L on day 9; M and N on day 12; O and P on day 14.

Figure 6:
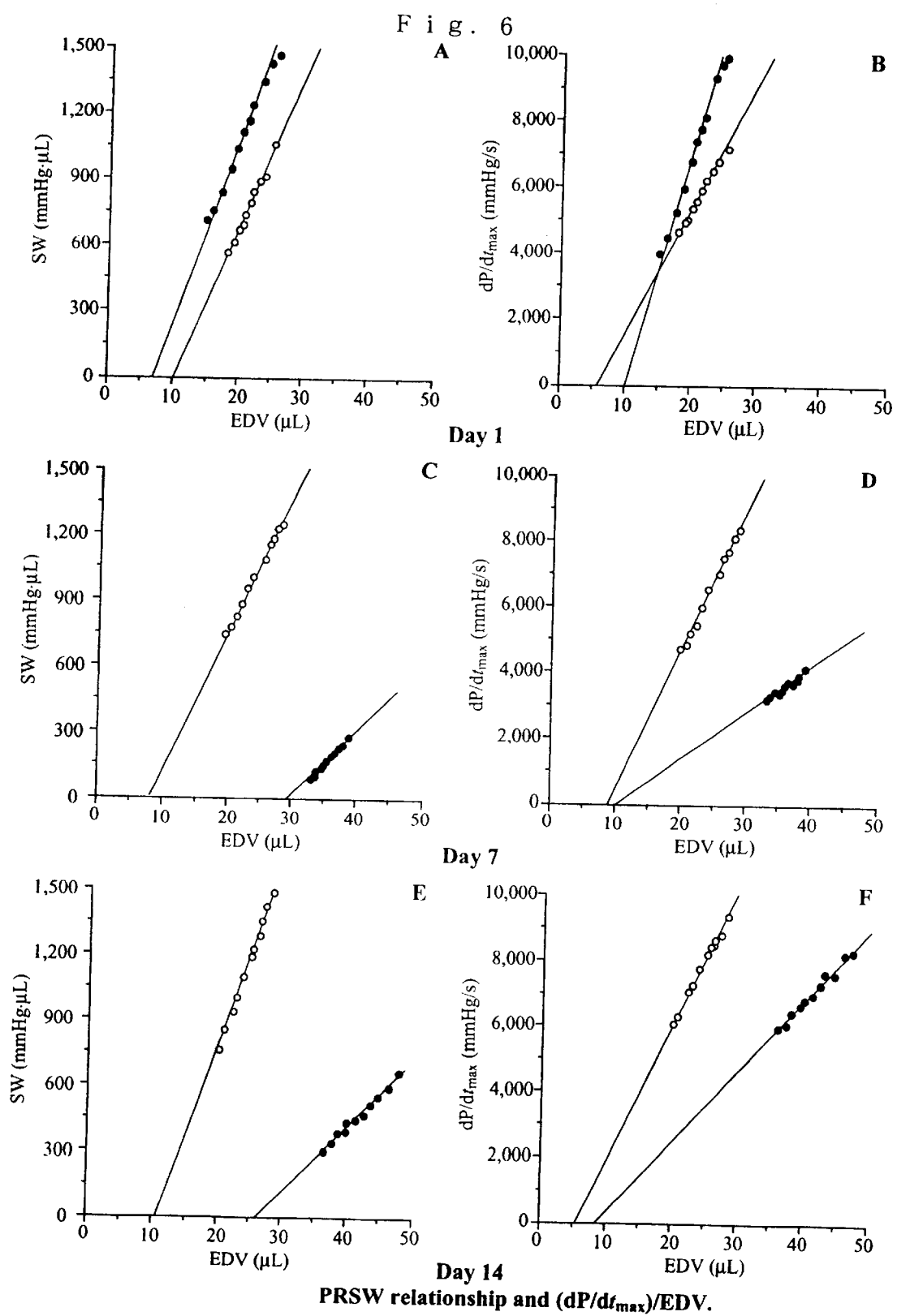
FIG. 6 shows PRSW relationship and $(dP/dt_{max})/EDV$ in Example 1.

FIG. 6 shows PRSW relationship and $(dP/dt_{max})/EDV$. A, C and E represent PRSW, and B, D and F do $(dP/dt_{max})/$ EDVA. A and B pertain to mice on day 1; C and D on day 7; E and F on day 14. ○ shows an uninfected control group, and ● does an infected group.

Figure 7:
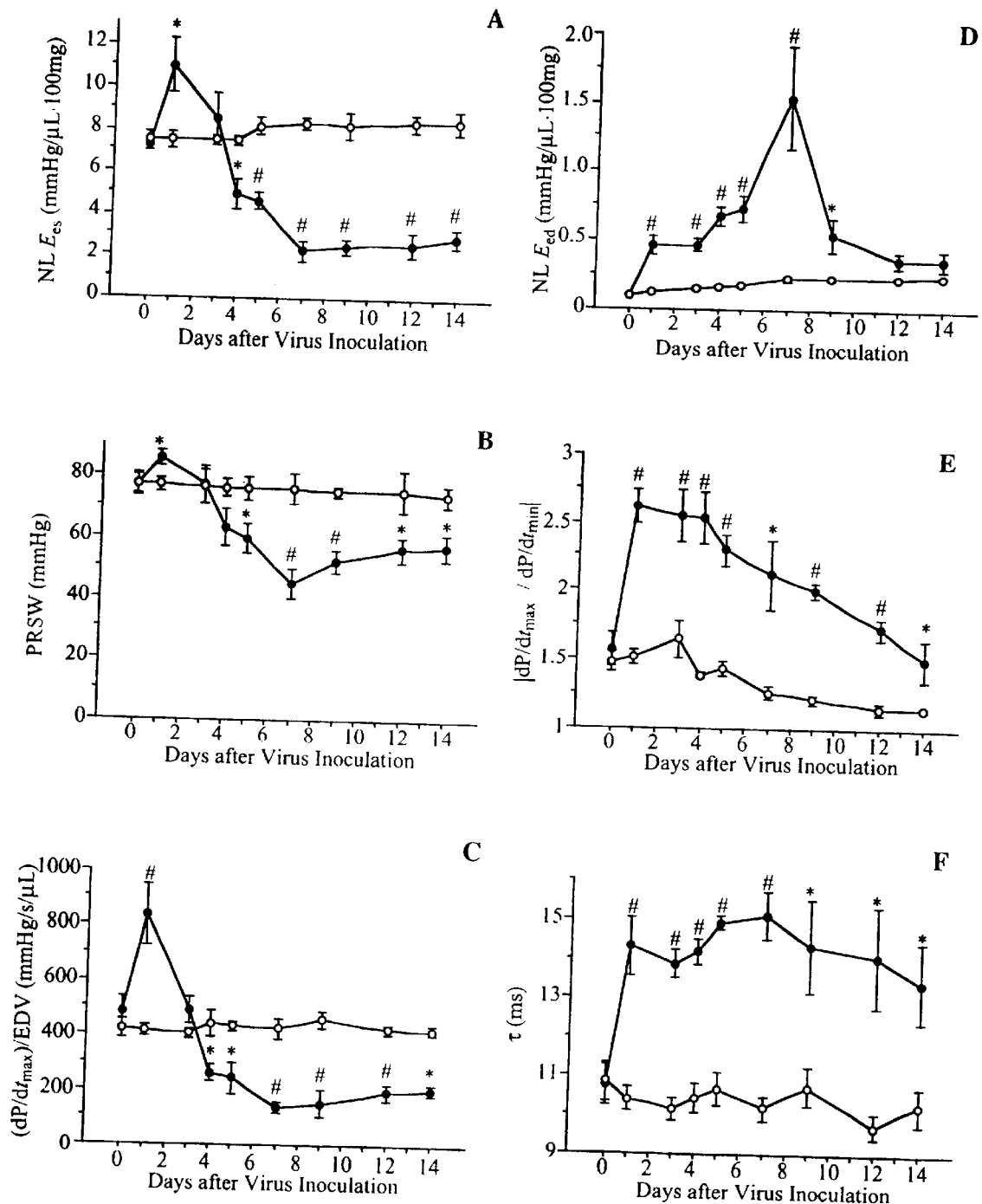
FIG. 7 shows evaluation results of respective hemodynamic variables in Example 1.
Figure 8:
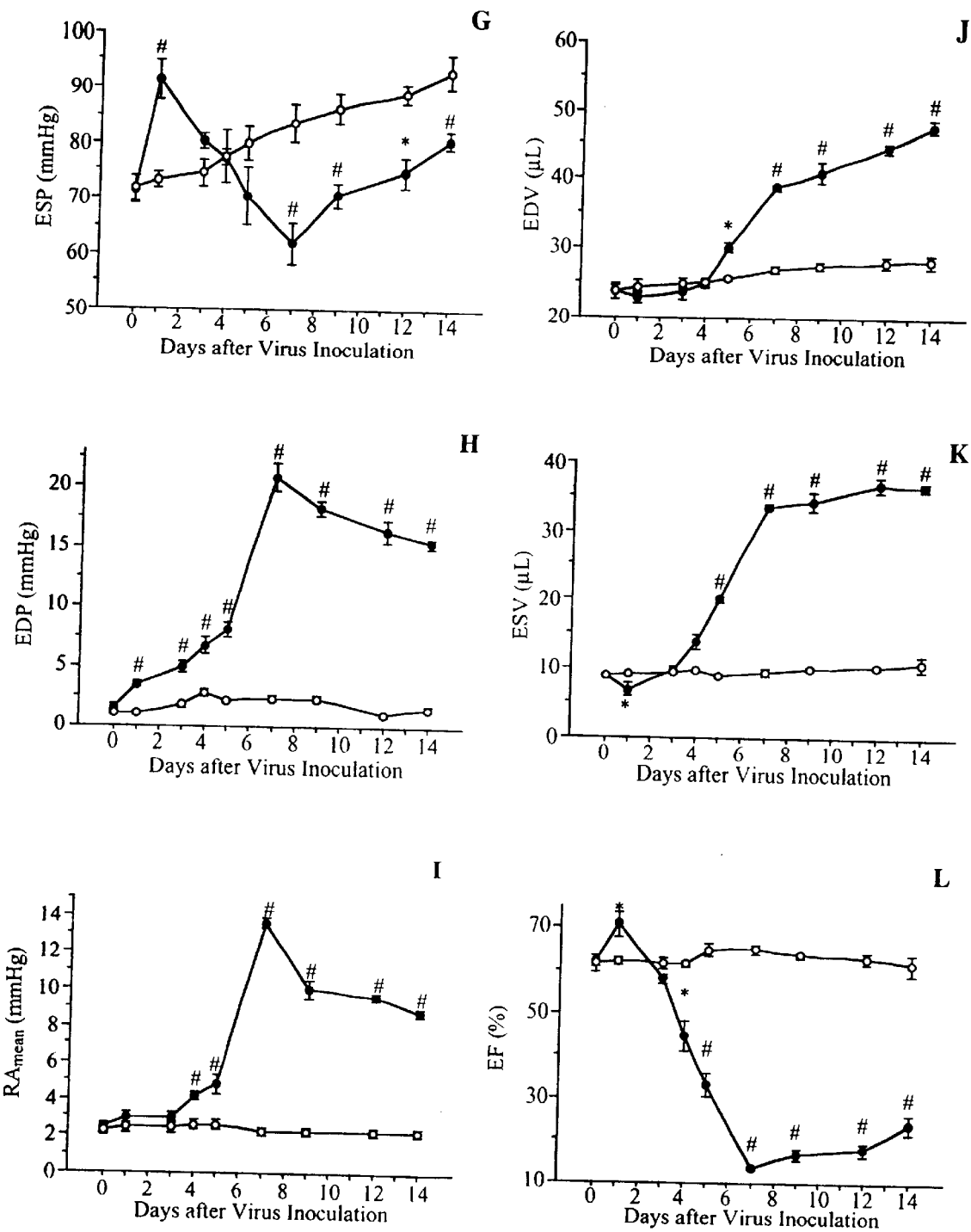
FIG. 8 shows evaluation results of respective hemodynamic variables in Example 1.
Figure 9:
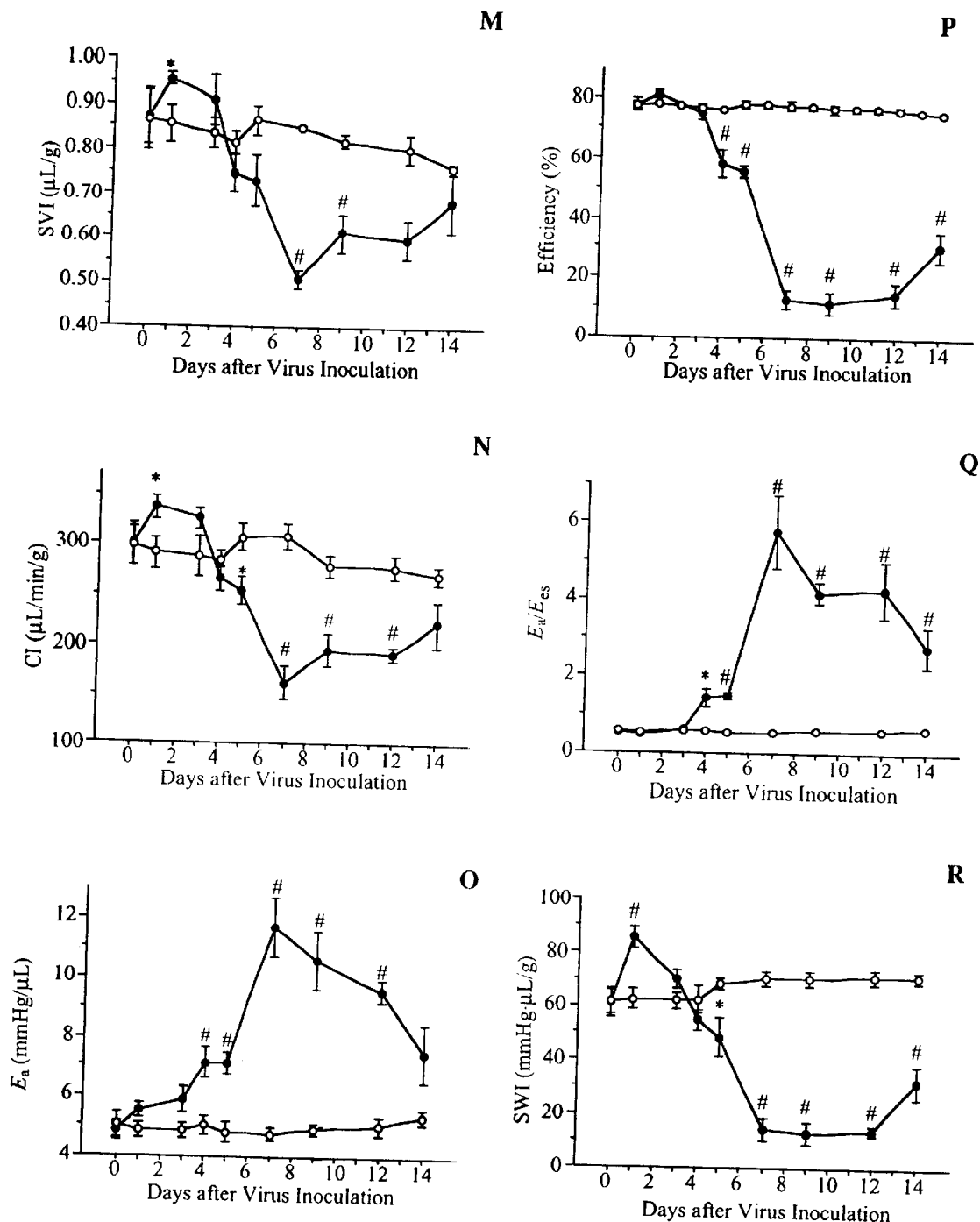
FIG. 9 shows evaluation results of respective hemodynamic variables in Example 1.

FIGS. 7 to 9 show evaluation results of respective hemodynamic variables. X-axis represents days after virus inoculation, and Y-axis does respective hemodynamic variables. ○ shows an uninfected control group, and ● does an infected group. For the control, * is p<0.05, and # is p<0.01. In each measurement, N is equal to 5.

Day 1

On day 1, at a stage when the hearts of infected mice show no gross pathologic changes, contractility was enhanced, diastolic function was abnormal, and EDP was increased in the group of infected animals (FIGS. 3A and B, and 6A and B). ESPVR in the infected mice had a markedly steeper slope in comparison with controls (FIG. 3A). The normalized $E_{es}$ (NL $E_{es}$) of the infected mice was significantly greater than that of the uninfected mice (p<0.05, table 1 and FIG. 5A). Consistent with the changes in ESPVR, PRSW (FIGS. 6A and 7B) and $(dP/dt_{max})/EDV$ (FIGS. 6B and 7C) in infected mice were significantly greater than in controls. $dP/dt_{max}$ and $dP/dt_{min}$ were significantly increased in the infected group (table 1 and FIG. 3B), although these 2 parameters vary with chamber volume, contractility, and HR. To normalize for these factors, $|dP/dt_{max}/dp/dt_{min}|$ (FIG. 7E), which is independent of preload and afterload, was calculated and was increased by approximately 72% in the infected compared with the uninfected mice. In addition, τ (FIG. 7F), an index of diastolic relaxation, was significantly longer in infected than in uninfected mice (p<0.01). Prolongation of χ and an increase in $|dP/dt_{max}/dP/dt_{min}|$ are both indicative of a delayed diastolic relaxation in the infected animals.

In addition to a delayed relaxation, chamber compliance was decreased in the infected group. FIG. 3A also shows a markedly steeper slope of EDPVR in the infected group in comparison with controls. Normalized $E_{ed}$ (NL $E_{ed}$) in the infected mice was significantly greater than in the uninfected mice (p<0.05; table 1 and FIG. 7D). EDP (table 1 and FIG. 8H) was significantly increased in the infected mice compared with controls (p<0.05), and EDV (table 1 and FIG. 8J) was decreased, though this difference was not statistically significant. ESP (table 1 and FIG. 8G) (p<0.01), ejection fraction (EF) (FIG. 8L), and SVI (FIG. 9M), and CI (FIG. 9N), were significantly higher in the infected group than in the uninfected group (p<0.05). Finally SVRI, an index of afterload, was significantly increased in the infected group (p<0.05, table 1).

Day 3

On day 3, a stage at which small foci of myocardial necrosis are found without evidence of cellular infiltration, abnormal diastolic function persisted in the infected mice, however without findings of enhanced contractility (FIGS. 3C and D). NL $E_{es}$, PRSW, and $(dP/dt_{max})/EDV$ were comparable in both groups. τ, $|dP/dt_{max}/dP/dt_{min}|$, $dP/dt_{min}$, and NL $E_{ed}$ were significantly increased in the infected mice as well as EDP (p<0.05). ESP, ESV (FIG. 8K), EDV, SVI, EF, CI, $dP/dt_{max}$, $RA_{mean}$ (FIG. 6I), and SVRI were comparable in both groups.

Day 4

On day 4, contractility began to fall in the infected mice (FIGS. 3E and F). NL $E_{es}$ and $(dP/dt_{max})/EDV$ of the infected mice were significantly lower than in the uninfected mice (p<0.05). Delayed diastolic relaxation persisted, and decreased chamber compliance further decreased. τ, $|dP/dt_{max}/dP/dt_{min}|$, and $dP/dt_{min}$ were significantly increased in the infected mice (p<0.01), along with NL $E_{ed}$, EDP, and $RA_{mean}$, compared with controls (p<0.01). EF was significantly lower (p<0.05), though SVI and CI were compensated by body weight loss. ESP, EDV, and $dP/dt_{max}$ were comparable in both groups.

Day 5

On day 5, decreased contractility and abnormal diastolic function had progressed, the chambers began to dilate, and cardiac output fell in the infected animals (FIGS. 4G and H). EDV and ESV were significantly greater in the infected than uninfected mice (p<0.05 and p<0.01, respectively). NL $E_{es}$, PRSW, $(dP/dt_{max})/EDV$, and $dP/dt_{max}$ had fallen significantly in the infected mice compared with the controls (p<0.05). In contrast, τ, $|dP/dt_{max}/dP/dt_{min}|$, $dP/dt_{min}$, NL $E_{ed}$, EDP, and $RA_{mean}$ had increased significantly. Finally, EF and CI were decreased in the infected group, while SVI and ESP were comparable in both groups.

Day 7

Changes consistent with heart failure culminated on day 7. Decreased contractility, abnormal diastolic function, chamber dilatation, and low output had each progressed in the infected mice (FIGS. 4I and J, and 6C and D). NL $E_{es}$, PRSW, $(dP/dt_{max})/EDV$, $dP/dt_{max}$, EF, ESP, CI, and SVI were significantly depressed in the infected compared with the uninfected mice. Accordingly, τ, $|dP/dt_{max}/dP/dt_{min}|$, and $dP/dt_{min}$ were significantly, and EDV, ESV, NL $E_{ed}$, EDP, and $RA_{mean}$ markedly increased in the infected mice compared with the controls.

Days 9 to 14

Abnormal systolic and diastolic dysfunction receded, though chamber dilatation progressed between day 9 and day 14 (day 9: FIGS. 4K and L; day 12: FIGS. 5M and N; day 14: FIGS. 5O and P, and 6E and F). Though ESP, EDP, ESV, EF, $dP/dt_{max}$, $dP/dt_{min}$, $|dP/dt_{max}/dP/dt_{min}|$, τ, NL $E_{es}$, PRSW, $(dP/dt_{max})/EDV$, $AO_{mean}$, $RA_{mean}$ each returned toward baseline between days 9 and 14, the differences between infected and infected groups on day 14 remained statistically significant. In contrast, SVI, CI and NL $E_{ed}$ returned toward baseline between days 9 and 14 to an extent such that the differences between infected animals and controls were no longer significant on day 14. EDV continued to increase past day 9 and, on day 14, remained significantly greater in the infected than in the uninfected mice.

SVRI remained comparable in both groups from day 3 to day 14 (table 1), while $E_a$ rose significantly between day 4 and day 12 in the infected group (FIG. 9O).

(C) Time Course of Efficiency of LV Work

Efficiency of LV work (SW/PVA) was depressed in the infected mice on day 4, when the contractility began to decrease (FIG. 9P). The fall in efficiency reached a nadir of 13.4±2.9% on day 7, in contrast to 78.6±1.4% in the uninfected group. Past day 9, the efficiency in the infected mice recovered, though remained significantly decreased on day 14 (p<0.05). Concordant with these measurements of efficiency, $E_a/E_{es}$ increased past day 4 in the infected mice, reached its peak on day 7, and recovered between day 9 and day 14 (FIG. 9Q). SWI was decreased on day 5 when CI began to decrease in the infected group, reached its peak on day 7, and recovered between day 9 and day 14 (FIG. 9R).

Discussions

Figure 10:
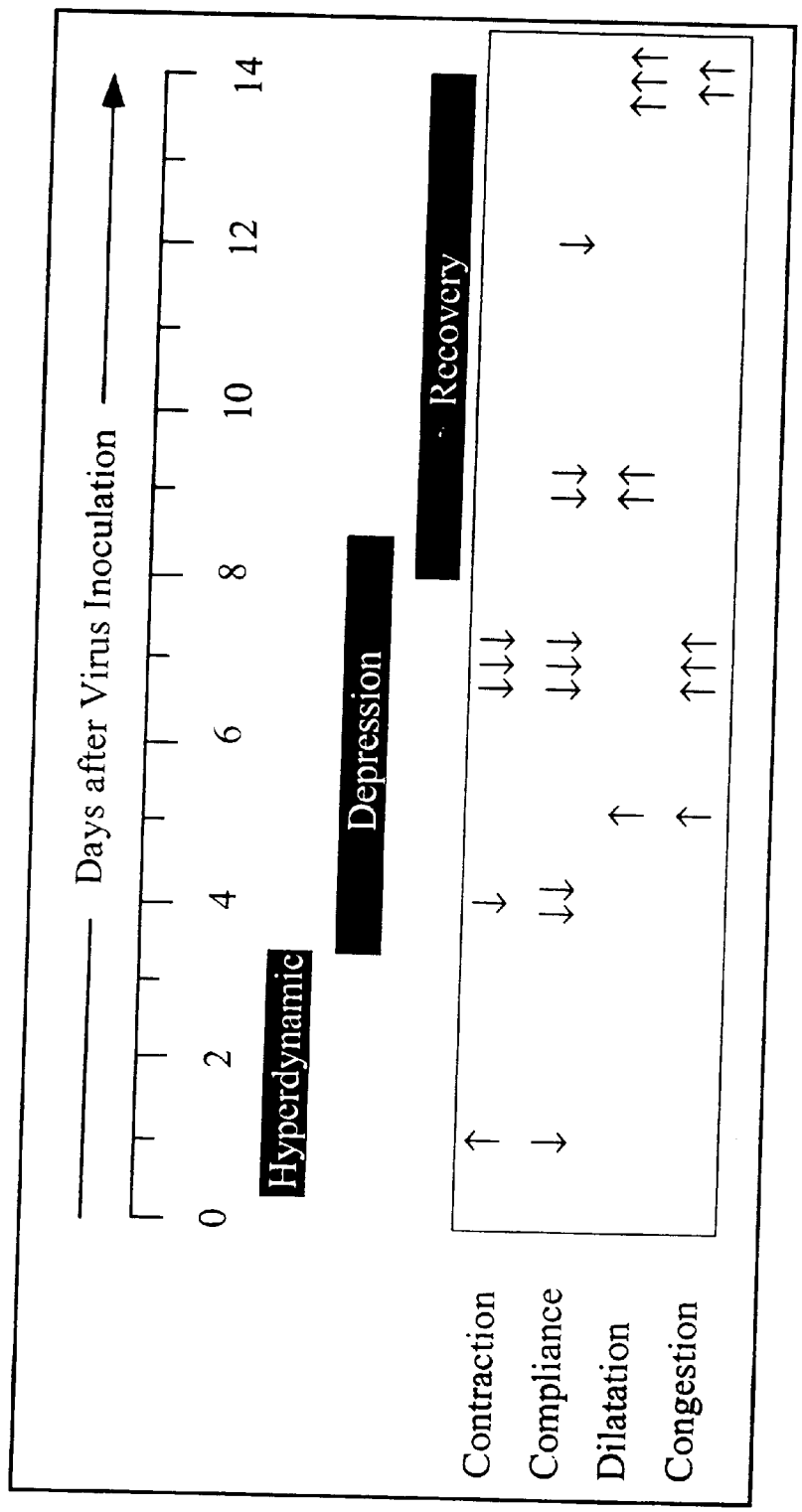
FIG. 10 shows pathologic manifestations during three phases of acute EMCV-induced myocarditis.

This study revealed that acute myocarditis induced by EMCV was characterized by 3 phases of hemodynamic evolution below (FIG. 10).

(1) A Hyperdynamic Phase

A hyperdynamic phase was observed from day 1 to day 3. In this phase, increases in contractility, cardiac output, ESP, and vascular resistance were observed, probably from activation of sympathetic activity, as has been described in another type of viral infection. A hyperdynamic state is often clinically observed in the hyperacute phase of myocarditis, though has not been specifically reported. It is noteworthy that diastolic dysfunction was found concomitantly. Abnormal relaxation and increased chamber stiffness were present, despite the known improvement in diastolic function expected from catecholamines. This diastolic dysfunction may be caused by direct viral activity. Murine cardiac troponin T is increased, and plaque assay shows the presence of EMCV in the myocardial homogenate as early as day 1 in this same model (ref. 13 and unpublished data). Trivial injury to the plasma membrane and myocardial structural proteins may be caused by the initial viral attack on the myocytes, despite the absence of gross pathologic abnormalities on day 1. Other immune mediators, including cytokines and proteins induced by EMCV, may cause this abnormal diastolic function.

(2) A Depressive Phase

A depressive phase was observed between day 4 and day 7, characterized by a progressive fall in contractility, lower cardiac output, impaired myocardial relaxation and decreased chamber compliance. LV dilatation was observed past day 5, while, on day 7, cardiogenic shock and severe congestion were documented in these experiments. Impaired contractility may be caused directly by myocyte injury and indirectly by nitric oxide and cytokines, including tumor necrosis factor-α and interleukin-1β. We have reported, in this model, the expression of mRNA of inducible nitric oxide synthase and of these cytokines, and the importance of these mediators in its pathophysiology. The expression of these cytokines was significantly increased on day 3 and peaked on day 7. Recent reports have emphasized the importance of nitric oxide and cytokines in the pathophysiology of congestive heart failure. The well-described direct and indirect negative inotropic effects of these immune-mediators are suspected to explain the decrease in myocardial contractility observed in this model. In addition, the progressive diastolic dysfunction occurring during this phase may be caused by myocytic injury, interstitial edema, and cellular infiltrations.

(3) A Recovery Phase

A recovery phase was observed between day 9 and day 14, during which contractility recovered slightly, and chamber compliance improved markedly. The decrease in contractility may have been caused by a fall in the production of nitric oxide and cytokines, while the improvement in chamber compliance may be explained by regressions in interstitional edema and inflammatory cellular infiltrations. Vascular resistance was not different between the 2 groups, perhaps because of production of nitric oxide and cytokines.

In conclusion, these hemodynamic observations made during the first 14 days of murine EMCV-induced myocarditis provide new insights into the pathophysiology of the acute phases of the disease, and may be useful in the development of therapeutic interventions.

According to the present invention, it is possible to provide a method for simultaneously and effectively measuring hemodynamics to evaluate pharmacological and therapeutic effects and so on in experimental animals.

Also, since the method according to the present invention is less invasive than the conventional opening-chest methods, it is possible to measure hemodynamics in experimental animals under less invasive and more physiological conditions than in the case of directly puncturing the heart of the animal.

According to the present invention, since hemodynamics can be measured more than once in a single individual of the experimental animal, it is possible to trace time-course hemodynamic changes, caused by medicine administration and so on, in a living body. Therefore, effects of medicines etc on the experimental animal can be measured more precisely. Also curative effects in the experimental animal as a disease model can be measured more strictly.

When the method according to the present invention is used, obtained measured values are comparative to those obtained by the conventional methods for measuring hemodynamics, and much higher measurement efficiency can be achieved.

Contraction ability, dilation ability and mechanical efficiency of the heart are hemodynamic parameters obtained only by simultaneous measuring pressure-volume of the heart. These parameters can be determined by hemodynamic data obtained by the method according to the present invention. These results also lead to evaluating a circulatory system. Moreover, useful data can be obtained in vivo to evaluate pharmacological effects of any medicines that are thought to have effects on the circulatory system.

In an animal larger than a rat weighing more than about 200 g, it is possible to simultaneously measure the pressure-volume of the heart in the conventional methods. However, in a mouse weighing about 20 g, the simultaneous measurement was impossible because of an excessive burden on the mouse. On the contrary, in the present invention, a subtle burden on the mouse makes it possible to simultaneously measure hemodynamics of the mouse as well.

Including a mutant mouse genetically engineered, there are many disease models which exist only in mice. One of the advantages in simultaneously measuring a blood pressure-volume according to the present invention is that regarding the disease models which exist only in mice, it is possible to determine not only a pharmacological effect but also a curative effect on diseases in living bodies. In other words, there is merit that it is possible to evaluate curative effects of medicines based on various parameters obtained from the blood pressure-volume simultaneous measurement, by simultaneously measuring the blood pressure-volume in, for example, a murine disease model of cardiac incompetence etc, including genetically engineering mice available at present.

What is claimed is:

1. A method for measuring hemodynamics of an experimental animal enabling repeated measurements, the method comprising the following steps:
   (i) ligating at least two parts of an artery, between which a part to be incised is located, of the experimental animal, the parts comprising at least one proximal ligated part and at least one distal ligated part, and then incising a part between the ligated parts;
   (ii) inserting through the incised part a blood pressure-volume simultaneously measuring catheter provided with multiple conductance electrodes and at least one pressure sensor;
   (iii) loosening the proximal ligated part so as to allow an insertion of the catheter and not to cause bleeding in the opened part;
   (iv) further inserting the catheter so as to introduce the multiple conductance electrodes and the pressure sensor(s) into the heart ventricle; and
   (v) simultaneously measuring pressure and volume of the heart.

2. The method according to claim 1, further comprising the following steps:
   (vi) pulling the catheter until a tip of the catheter is positioned between the proximal ligated part and the incised part;
   (vii) ligating the proximal ligated part to such an extent as to prevent bleeding in the opened part after the catheter is completely pulled out;
   (viii) pulling out the catheter and suturing the opened part; and
   (ix) untying the proximal ligated part and the distal ligated part.

3. The method according to claim 1, wherein the artery of the experimental animal is cranial to the heart.

4. The method according to claim 3, wherein the artery cranial to the heart is a carotid artery.

5. The method according to claim 1, further comprising a step of investigating time-course of hemodynamics by repeatedly measuring hemodynamics in a single individual animal.

6. The method according to claim 1, wherein in the step (i), ligating three parts of the artery, among which a part to be incised is located, the three parts being two proximal ligated parts and a distal ligated part, and in the step (iii), loosening the two proximal ligated parts.

7. The method according to claim 1, wherein the experimental animal is a mouse.

* * * * *